(12) United States Patent
Rautenbach

(10) Patent No.: US 6,901,884 B1
(45) Date of Patent: Jun. 7, 2005

(54) IMMOBILIZATION DEVICE

(76) Inventor: Abel Jacobus Rautenbach, Avoca, Reitz, Free State (ZA)

( * ) Notice: Subject to any disclaimer, the term of this patent is extended or adjusted under 35 U.S.C. 154(b) by 137 days.

(21) Appl. No.: 09/671,607

(22) Filed: Sep. 28, 2000

Related U.S. Application Data

(60) Provisional application No. 60/156,597, filed on Sep. 29, 1999.

(51) Int. Cl.[7] ......................... A01K 15/00; A01K 15/04
(52) U.S. Cl. ........................... 119/719; 119/908; 231/7
(58) Field of Search ................... 119/712, 719, 814, 119/838, 854, 908; 607/138; 361/232; 231/7

(56) References Cited

U.S. PATENT DOCUMENTS

| | | | |
|---|---|---|---|
| 2,085,644 A | * | 6/1937 | Ferciot ........................ 607/138 |
| 3,403,684 A | * | 10/1968 | Stiebel et al. ................ 331/111 |
| 3,933,147 A | * | 1/1976 | Du Vall et al. ............. 600/591 |
| 4,092,695 A | * | 5/1978 | Henderson et al. ............ 231/7 |
| 4,909,263 A | * | 3/1990 | Norris ......................... 600/551 |
| 5,199,442 A | * | 4/1993 | Seager et al. ................ 600/547 |
| 5,233,987 A | * | 8/1993 | Fabian et al. ................ 600/587 |
| 5,370,671 A | * | 12/1994 | Maurer et al. .............. 607/138 |
| 5,385,577 A | * | 1/1995 | Maurer et al. .............. 607/138 |
| 5,411,548 A | * | 5/1995 | Carman ...................... 600/546 |
| 5,499,631 A | * | 3/1996 | Weiland ...................... 600/547 |
| 5,662,699 A | * | 9/1997 | Hamedi et al. ............. 607/138 |
| 6,091,597 A | * | 7/2000 | Lin ............................. 361/115 |

FOREIGN PATENT DOCUMENTS

| | | | | |
|---|---|---|---|---|
| AU | 729373 B | * | 2/2001 | .......... A01K 14/00 |
| DE | 3305661 A | * | 8/1984 | .......... A01K 15/02 |

* cited by examiner

*Primary Examiner*—Son T. Nguyen
(74) *Attorney, Agent, or Firm*—Banner & Witcoff, Ltd.

(57) ABSTRACT

The invention provides a device for use in partially or fully immobilizing animals such as cattle, sheep and the like. The device includes a probe for insertion in the anal canal of the animal the probe comprising a pair of spaced electrodes connected by way of electrical conductors to a power source. The power source providing a pulsed electrical current having a voltage of between 2 and 10 Volts and a frequency of between 20 and 50 Hz to the electrodes.

4 Claims, 1 Drawing Sheet

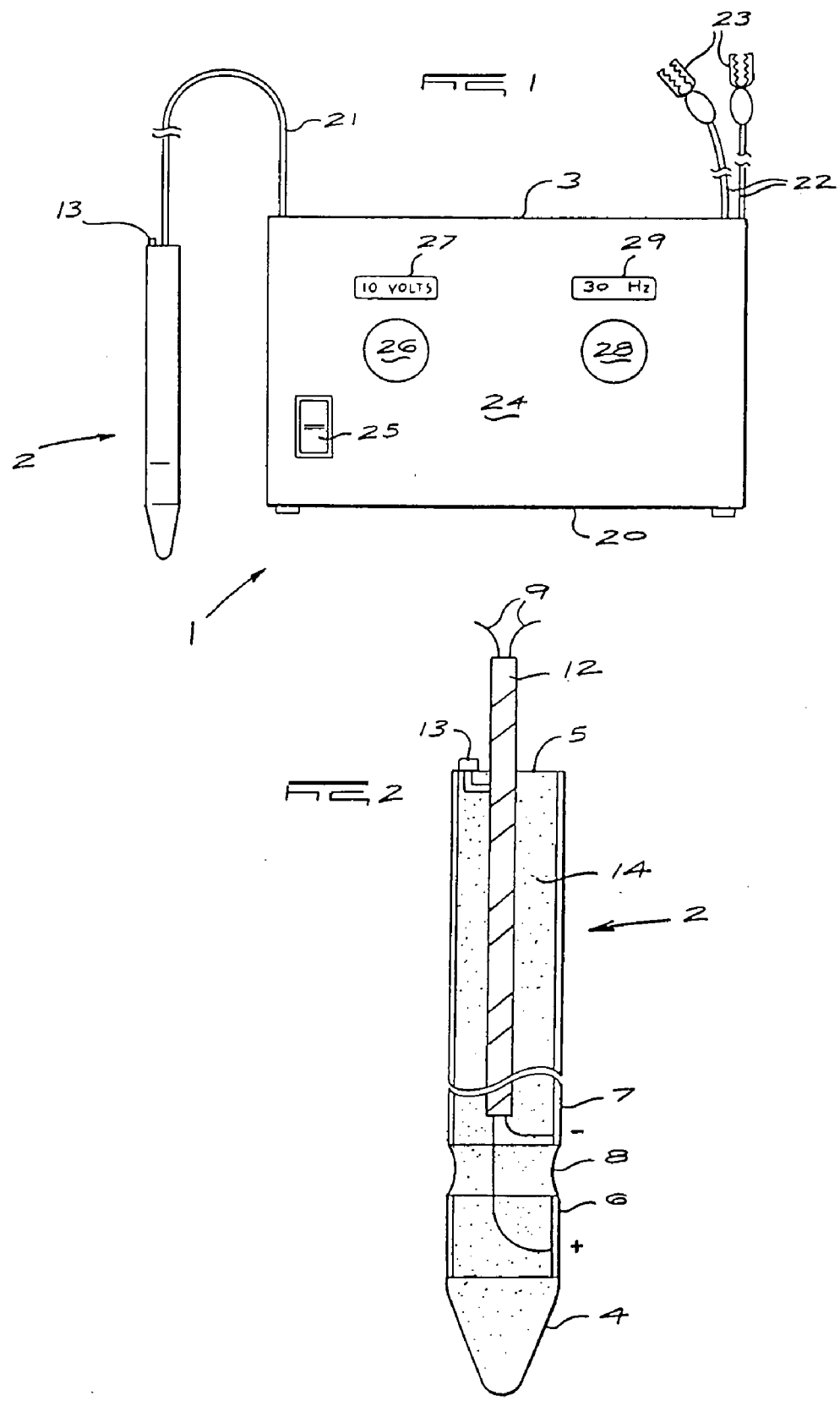

IMMOBILIZATION DEVICE

Benefit of the Sep. 29, 1999 filing date of the provisional application Ser. No. 60/156,597 by the same inventor and entitled "Immobilisation Device" is hereby claimed.

INTRODUCTION TO THE INVENTION

This invention relates to a device for use in partially or fully immobilising animals.

BACKGROUND TO THE INVENTION

Immobilization of animals is necessary in order to perform a variety of operations on them. These include slaughtering, medical procedures, identification procedures and the like.

Various methods are known for achieving immobilisation. Amongst these and relevant to this invention is the application of electrical currents to nerves to interfere with their function. Such application may be via electrodes placed on the skin of the animal.

OBJECT OF THE INVENTION

An object of this invention is to provide a device for the application of electrical currents to animals for the purpose of immobilising them.

SUMMARY OF THE INVENTION

According to the invention a device for use in immobilising animals comprises an elongated probe having a rear end and a front end for insertion into the anal canal of an animal, the probe having first and second electrodes spaced from each other on the outer surface thereof and electrical conductors extending from the electrodes and adapted for connection to an electrical power source.

Further according to the invention the elongated probe is of right circular cylindrical configuration with the front end being a tapered rounded tip.

Still further according to the invention the first electrode is of annular configuration and is located near the front end of the probe and the second electrode is of annular configuration and is located near to the first electrode.

Still further according to the invention the first and second electrode are separated by an annular groove in the probe.

Still further according to the invention the second electrode extends from a position near the first electrode to the rear end of the probe.

Still further according to the invention the electrodes are stainless steel electrodes.

Still further according to the invention the first electrode is a positive electrode and the second electrode is a negative electrode.

Still further according to the invention there is an indicator light at the rear end of the probe.

Still further according to the invention the device includes a power source for connection to the electrical conductors and hence the electrodes, the power source being adapted to supply a pulsed or alternating electrical current to the electrodes, the electrical current being between about 250 and 400 mA and having a voltage of between 1 and 11 volts and a frequency of between 20 and 50 Hz.

Still further according to the invention the voltage is between 2 and 10 volts and the frequency is about 30 Hz.

The invention also provides a method of immobilising an animal which includes inserting a probe having a pair of electrodes into an animal's anal canal and applying an electrical current through the electrodes.

Further features of the invention provide for the electrical current to be pulsed or alternating; for the current potential to be between 1 and 11 volts, preferably between 2 and 10 volts; for the frequency to be between 20 and 50 Hz, preferably 30 Hz; and for the current to be between about 250 and 400 mA.

BRIEF DESCRIPTION OF THE DRAWINGS

One embodiment of the invention described by way of example only follows with reference to the accompanying drawings in which:

FIG. 1 is a general elevation of a device according to the invention; and

FIG. 2 is a sectional elevation of the probe of the device.

DETAILED DESCRIPTION WITH REFERENCE TO THE DRAWINGS

In this embodiment of the invention a device (1) for use in immobilising animals, especially domestic ungulates such as cattle, sheep, goats and the like is provided.

The device (1) comprises a probe (2) for insertion in the anal canal of the animal and a power source (3) to which the probe is connected.

As may be seen from FIG. 2 the probe (2) is elongated and is basically right circular cylindrical in shape with a tapered rounded front end (4) and a substantially flat circular rear end (5). The body of the probe is made from an electrically insulating material which is preferably a cast settable material such as an epoxy.

The probe (2) comprises a first electrode (6) and a second electrode (7). The first electrode (6) is an annular stainless steel electrode which is relatively short in length and which is located adjacent the tip (4) of the probe (2). This is the positive electrode. The second electrode (7) is an annular stainless steel electrode which is co-axial with the first electrode (6) and separated therefrom by means of a shallow annular groove (8). This second electrode is much longer that the first electrode (6) and in fact constitutes the major portion of the length of the probe.

Within the probe are a pair of electrical conductors (9) which extend from the first and second electrodes (6) and (7) through a sheath (12) extending generally co-axially along the length of the probe and emerging form the rear end (5) thereof.

At the second end (5) of the probe is a small light emitting diode (13) which is connected to the electrical conductors (9) and which is adapted to indicate whether there is an electrical potential across the two electrodes (6) and (7).

The internal body (14) of the probe (2) is made from a settable insulating material so that the two electrodes (6) and (7) with the electrical conductors (9) and sheath (12) can be cast into an integral unit.

The power source (3) for supplying a pulsed current to the probe (2) is shown in FIG. 1 and includes a housing (20) which houses electronic circuitry designed in accordance with the function it is to perform and which is not shown or described in any further detail in this specification.

The power supply is connected as shown by cable (21) embodying the conductors (9) to the probe (2). Power for the power source is preferably from a 12 volt motor car battery and leads (22) are provided for connecting the power source to such a battery. The leads are provided at their ends with suitable clamps (23) for connecting to battery terminals.

The power source (3) has a front face (24) which incorporates and on/off switch (25) with an integral light which indicates whether the power supply is on.

Two dial type controls are provided. The first dial control (26) adjusts the voltage of the electrical supply to the probe (2) this voltage usually being between 2 and 10 Volts. The voltage is indicated by means of an LED display (27) above the dial (26).

The second dial (28) is used to adjust the frequency of the pulses of the electrical current supplied to the probe and the value of this frequency is indicated on an LED display (29) above the dial (28). A frequency of between 20 and 50 Hz has been found to be effective.

In use the power supply (3) is connected to a 12 Volt direct current source such as a car battery. A current of between about 250 mA to 400 mA has been found to work effectively. Currents lower than about 250 mA are not very effective while those above 400 mA have been found to be excessive.

The probe (2) is inserted into the anal canal of an animal which is intended to immobilise. The power supply is turned on and the voltage and frequency of the current supply to the probe is adjusted in the above ranges to give the degree of immobility required. The invention thus provides a device which can be beneficially used in the immobilising of animals for procedures such as medical procedures, branding and the like.

Other embodiments are envisaged within the scope of the invention which includes other configurations and constructions thereof.

What is claimed is:

1. A method of immobilizing a non-human animal comprising the steps of:
    (a) inserting a probe having a pair of electrodes into the anal canal of the animal; and
    (b) applying a pulsed electrical current through the electrodes to the animal, said current having a frequency of between about 20 and 50 Hz, a potential of between about 1 and 11 volts and a current strength of between about 250 and 400 mA.

2. A method of immobilizing an animal as recited in claim 1 wherein the applying a pulsed electrical current step includes applying an electrical current having a frequency of about 30 Hz.

3. A method of immobilizing an animal as recited in claim 1 wherein the applying a pulsed electrical current step includes applying an electrical current having a potential of between about 2 and 10 volts.

4. A method of immobilizing an animal as recited in claim 1 wherein the animal is an ungulate.

* * * * *